United States Patent [19]
Kauvar

[11] Patent Number: 6,057,092
[45] Date of Patent: May 2, 2000

[54] CELLULAR TRANSPORT DETECTION METHOD

[75] Inventor: Lawrence M. Kauvar, San Francisco, Calif.

[73] Assignee: Trellis Bioinformatics, Inc., San Francisco, Calif.

[21] Appl. No.: 09/144,609

[22] Filed: Aug. 31, 1998

[51] Int. Cl.[7] ............................... C12Q 1/00; C12Q 1/16
[52] U.S. Cl. .................................. 435/4; 435/35
[58] Field of Search ............................ 435/35, 4

[56] References Cited

U.S. PATENT DOCUMENTS

| | | | |
|---|---|---|---|
| 4,382,074 | 5/1983 | Hart | 436/537 |
| 4,418,052 | 11/1983 | Wong | 424/1.1 |
| 4,568,649 | 2/1986 | Bertoglio-Matte | 436/534 |
| 4,634,586 | 1/1987 | Goodwin et al. | 424/1.1 |
| 4,687,636 | 8/1987 | Hart | 422/57 |
| 5,246,869 | 9/1993 | Potter et al. | 436/518 |
| 5,512,753 | 4/1996 | Thomson et al. | 250/361 R |
| 5,627,381 | 5/1997 | Kulpinski | 250/588 |
| 5,665,562 | 9/1997 | Cook | 435/35 |

OTHER PUBLICATIONS

Bosworth et al. "Scintillation proximity assay", Nature, Sep. 14, 1989, vol. 341, pp. 167–168.

*Primary Examiner*—Sandra E. Saucier
*Assistant Examiner*—Vera Afremova
*Attorney, Agent, or Firm*—Morrison & Foerster LLP

[57] ABSTRACT

A method to follow the uptake of labeled materials into scintillant-marked compartments, cells, tissue and organelles in real time by monitoring the location of scintillant-emitted light is disclosed.

18 Claims, No Drawings

CELLULAR TRANSPORT DETECTION METHOD

TECHNICAL FIELD

The invention relates to methods to detect the transport of compounds across cellular barriers in biological systems. More precisely, the invention concerns a microscope-based method for visualizing the transport of radioactively labeled compounds through cells, tissues or organelles that have been associated with a scintillant.

BACKGROUND OF THE INVENTION

Scintillation counting of a beta emitting radioactive isotopes is a standard method of measuring the level of a labeled substance. Scintillation counters are commercially available for such analysis. As disclosed in U.S. Pat. No. 5,512,753, a number of techniques are available for providing a scintillant. These include solid scintillators comprising crystals of a solid hydrocarbon material; liquid scintillators which have one or more solid scintillators dissolved in a liquid solvent; solid solution scintillators wherein a solid scintillator is embedded in a solid polymer and solid scintillators which comprise crystals of a suitable inorganic material. To this list, the '753 patent adds encapsulated scintillators which include a liquid scintillator core within a shell.

Applications of scintillation counting incorporated into specifically designed assays have been termed "scintillation proximity assays." These depend on the necessity for the scintillant to be within a certain distance of a beta emitting radioactive isotope in order to emit light; the mean radiation distance of the beta emitter determines the distance required for the scintillant to emit detectable light. By associating the scintillant with a reagent to be tested against a labeled substance, the interaction of the substance with reagent can be assessed. Either the analyte bears a beta emitting radioisotope, or is placed in competition with a labeled form or analog of the analyte for the reagent associated with scintillant. Such assays are described generally in U.S. Pat. Nos. 4,382,074; 4,568,649; and 4,687,636. A typical approach involves a homogeneous immunoassay system wherein a scintillant is embedded in a particulate bead which is conjugated to an antibody. Substances immunoreactive with the antibody can be measured by competition with a radioactively labeled form of the substance or its analog for the antibody coupled to the beads; the level of light emitted by the scintillant is thus inversely proportional to the analyte in the sample.

A refinement of this concept is disclosed in U.S. Pat. No. 5,246,869, wherein several ligands can be assayed simultaneously. This assay employs two or more different scintillants which can be distinguished by their emission spectra, each attached to different reagents which specially bind different ligands.

U.S. Pat. No. 5,665,562, incorporated herein by reference, describes a scintillation based system for monitoring uptake of radioactively labeled substrates by cellular monolayers. In this macroscopic method, a modified form of a 96-well microtiter plate is employed, whereby a region of the base portion of the wells is constructed of polystyrene containing a scintillant, such as 2-(4-t-butylphenyl)-5-(4-biphenylyl)-1-3,4-oxadiazole (2%) and 9,10-diphenylanthracene (0.5%). The plate is constructed so as to minimize or eliminate the passage of light from well to well. A monolayer of cells is coated in each well and the uptake of a radioactively labeled substrate is measured by the emission of light by the scintillant.

In addition, digital systems for readout and storage of emission of radiation have been described in U.S. Pat. No. 5,627,381.

However, to applicant's knowledge, the use of scintillants embedded in cells, tissues or organelles to follow the behavior of compounds labeled with beta emitting isotopes at microscopic resolution has not been previously employed. The availability of wide-field microscopy for observing emitted light with high resolution enhances this possibility, though ordinary microscopic techniques may also be used.

DISCLOSURE OF THE INVENTION

The invention provides a method for direct observation of the behavior of a compound labeled with a beta emitter with respect to locations in a biological sample. This permits assessment of the bioavailability of test compounds, as well as the ability of other, unlabeled compounds to affect bioavailability of the compounds which are thus labeled. Thus, the materials and methods of the invention can be used, for example, to evaluate the effect of test substances on the oral availability of drugs or on the cellular uptake of metabolites.

In one aspect, the invention is directed to a method to determine the location of a compound as a function of time with respect to a compartmentalized biologically derived environment which method comprises providing a cell, tissue or organelle marked with a scintillant in a first compartment to the exclusion of a second compartment; positioning said a scintillant-marked cell, tissue or organelle on the stage of a microscope focused on the marked compartment; contacting the unmarked compartment of said cell, tissue or organelle with a test compound labeled with a beta emitting radioactive isotope and observing the appearance of scintillant emitted light in said marked compartment as a function of time. Conversely, the cells optionally contained in a tissue or organelle and marked with a scintillant may be provided with amounts of labeled compound in the marked compartment and the efflux of the labeled compound from the marked compartment can be followed by the diminution of scintillation emissions.

In one embodiment, the marked compartment is the intracellular environment and the unmarked compartment comprises its surroundings.

In another aspect, the invention is directed to a method for determining the effect of a test substance on the transport (influx or efflux) of a compound labeled with a beta emitting radioisotope in a compartmentalized biological sample which method comprises providing a cell, tissue or organelle marked with a scintillant in a first compartment to the exclusion of a second compartment, placing the scintillant-marked cells, tissue or organelle on the observation stage of a microscope focused on the marked compartment, and contacting the unmarked compartment of the cells or tissue with the test substance and the compound labeled with a beta emitting radioisotope. The emission of light from the scintillant at various locations in the cell or tissue as a function of time is then observed. If desired, the pattern of emission thus observed can be compared with that observed in the absence of the test substance. Again, conversely, the beta emitter labeled compound may be placed initially in the marked compartment, the sample and its efflux observed in the presence and, if desired, the absence of the test substance.

MODES OF CARRYING OUT THE INVENTION

Applying scintillation proximity assays to a microscopic format using appropriately small amounts of sample tissue or cells and correspondingly small amounts of test compounds and other reagents permits real time observation of transport of compounds across cellular membranes and of the effect of potential enhancers or inhibitors on this transport.

One specific application of the present technique is in the study of oral availability of drugs. It is believed that oral availability is governed by the ability of intestinal epithelial cells to reject orally administered compounds by action of efflux pumps. This mechanism has been described in U.S. Pat. No. 5,716,928 which proposes the use of essential oils to overcome this process. A related patent U.S. Pat. No. 5,567,592 describes and claims a screening method for bioenhancers by determining their ability to inhibit P-glycoprotein transport activity in the gut. P-glycoprotein is said to be responsible for backflow of compounds which have diffusively entered the gut epithelial cells from the intestinal lumen. According to the assay methods described in the '592 patent, an iii vitro determination can be made by using everted intestine wherein the intestine is turned inside out so that the mucosal or luminal surface is turned outside and the serosat surface is turned inside. The passage of a dye, such as rhodamine is followed from the luminal surface (now on the outside) to the serosat surface (now on the inside) in the presence and absence of a test substance. A substance which enhances the flow of rhodamine from the lumen to the serosat solution contained inside the everted intestine is shown to be an enhancer.

A cellular assay is also described whereby cells are loaded with rhodamine dye and the efflux of the dye from the cells monitored by fluorescence in the presence and absence of a test substance. Reduction of the efflux in the presence of a test substance indicates that that substance is a P-glycoprotein inhibitor. Additional assays are also described, all of which require macroscopic samples and all of which require the use of a model irrelevant compound, such as the dye, to stand in for the drug whose bioavailability is to be influenced. This adds an additional variable in interpreting the results with regard to the test substance.

The present invention overcomes these difficulties by permitting the use of the actual drug whose availability is to be explored provided it can be appropriately labeled with a beta emitting radioactive atom. This is generally possible since suitable labeling radioactive atoms include those useful in compounds of biological interest Beta emitting radioisotopes having sufficiently low energy radiation that proximity to the scintillant is required for light emission must be used. These isotopes include tritium, $^{125}I$, $^{14}C$, $^{35}S$, $^{45}Ca$, $^{33}P$ and $^{32}P$ as well as $^{55}Fe$, $^{109}Cd$ and $^{51}Cr$. It may be of interest that mean path lengths of several of these isotopes are provided in U.S. Pat. No. 5,665,562. They can be summarized as follows:

| Isotope | Form | Mean Distance Traveled into Mammiatain cells ($\mu$m) |
| --- | --- | --- |
| $^3H$ | L-[methyl-$^3$H]methionine | 1.5 |
| $^{14}C$ | L-[methyl-$^{14}$C]methionine | 58 |
| $^{35}S$ | L-$^{35}$S methionine | 66 |
| $^{33}P$ | orthophosphate | 126 |
| $^{32}P$ | orthophosphate | 1600 |
| $^{45}Ca$ | CaCl$_2$ | 131 |
| $^{145}I$ | 5-iodo-2-uridine | 17 |
| $^{51}Cr$ | Na$_2$ CrO$_4$ | 890 |
| $^{109}Cd$ | CdCl$_2$ | 104 |

Theoretically, therefore, any organic compound can be appropriately labeled by incorporating, for example, tritium or $^{14}C$, and compounds which contain the additional biologically relevant isotopes listed above can also be employed.

One particularly useful application, in view of the availability, for example, of labeled ions is exploration of the functions of the transport across ion pumps. In this application, one side of the pump is painted with a scintillant and the other is not. The transit of the ion through the channel could then be measured by the appearance of visible radiation. This can readily be applied in vivo for physiological testing of the ability of these pumps to function. For example, the defective ion channel responsible for cystic fibrosis can be studied in this way.

In addition to the advantage of permitting the use of any compound of interest in these cell based assays, the adaptation of this technique to use in microscopy permits the behavior of a radioactively labeled compound to be directly observed with respect to the treated cell, tissue or organelle. Variation in uptake propensity across the length of the gut can thereby be examined. While any light microscope configuration can be used, wide-field microscopy is preferred since it can resolve fine details even in thick specimens (~100 $\mu$m) and has high sensitivity. Thus, a thin coating of scintillant may be used to mark the relevant compartment. Further, computational processing can reject most extraneous light. A suitable instrument is available from Applied Precision, Inc., Seattle, Wash.

For use in the method of the invention, the small sample of biological material is painted in the marked compartment with the scintillant by precipitating the scintillant as a fine suspension in agarose or other convenient carrier. Alternatively, thin slices of tissue can be bathed in a solution or suspension of scintillant optionally in the presence of a carrier to label the cells therein—the cells themselves thus comprising the marked compartment. Suitable tissues include brain, lung, skin, capillaries, liver, neuronal tissue and gut. The behavior of specific compounds with respect to these tissues can then be studied directly.

A number of materials can be used to provide the scintillant. If suitably small particles can be obtained, lanthanide containing glasses can be used. Alternatively, organic phosphors can be embedded in polymers such as polystyrene, polyvinyltoluene and polyacrylates. Various aromatic hydrocarbons can be used as scintillants. A large array of suitable organic compounds useful as scintillants is known in the art.

By marking particular compartments of the cells or tissue as described above, the path of a suitably labeled molecule within the cell or tissue can be followed. By "labeled" is meant that the compound includes a radioisotope that emits beta radiation of sufficiently low energy that proximity to within a desired distance of the scintillant is required before significant light emission occurs. In general, a shorter mean free path of the radiation provides the opportunity for finer resolution. However, in many instances, an arbitrary distance of the probe from the β-emitting atom can be managed. For example, a fiber-optic probe painted with scintillant can be used to scan over tissue to pick up the location of label. The distance of the painted tip of the fiber-optic from the labeled compound is, in this instance, arbitrary.

In one embodiment, after a cell or cell contained in a tissue has been marked with the scintillant, it is placed on an observation stage of a wide-field microscope for observation. The surroundings of the tissue are then provided with a suitably labeled compound whose transport through the cells or tissue is to be evaluated. Direct observation permits a real time description of the behavior of the labeled compound with respect to the cells. In addition, a test substance which is to be evaluated for its ability to influence the transport of the labeled compound is added to the surroundings as well. A comparison of the behavior of the labeled compound in the presence or absence of the test substance identifies the substance as an enhancer, inhibitor, or neutral with respect to the influx or efflux of the test compounds relative to the cells.

By "surroundings" is meant the medium contacting the cells or tissue on the observation stage.

In another embodiment related to the foregoing, the cells are provided the labeled compound intracellularly by permitting uptake of the labeled compound prior to observation. The scintillant may be supplied before or after intracellular uptake is effected. The observation is then conducted in a similar manner in the presence or absence of substance to be tested for is enhancing or inhibiting ability with respect to transport.

As described above, the observations permitted by the method of the invention are of particular interest in evaluating oral availability of drugs, which can be thus used in the assay as the labeled compound. Potential inhibitors of efflux or enhancers of influx of these labeled compounds into epithelial cells of the gut then can be used to enhance bioavailability. The assays described above with respect to everted gut tissue can be more simply performed using the method of the invention thus viewing the transport of compounds through epithelial cells in the presence and absence of test substance if desired.

U.S. Pat. No. 5,254,342 describes studies of enhancing transcellular or transmembrane transport of an active agent which is coupled to the ligand for the transferrin receptor by administering the conjugate with a transfer enhancing agent such as brefeldin A or monensin. It is thus possible to provide a system of standardized capability for transfer across the transepithelial surface whereby the effects of various compounds on the transport baseline can be evaluated. In a control, standardized form of the invention assay, a thin slice of gut tissue, painted with a suitable scintillant is placed on the microscope observation stage and treated with radioactively labeled transferrin conjugate as described in the '342 patent in the presence of a transport enhancer. Rather than a gut tissue itself, the known model provided by the Caco-2 cell line grown as a continuous sheet on a membrane can be substituted. Since brefeldin A and monensin are shown in the '342 patent to be enhancers, use of these compounds can serve as a positive control. The transport of the radioactively labeled conjugate across the transepithelial surface is then observed in the presence and absence of a substance that is a candidate for enhancing uptake. An enhancement of transport in the presence as compared to the absence of compound indicates that it is a useful agent to improve oral availability in a formulation.

Materials shown to enhance influx or inhibit efflux of labeled compounds in the gut epithelium can then be provided in the context of drug formulations or by administering them separately, preferably attached to latex beads, polyethylene glycol or other pharmaceutically acceptable polymers so that they will be retained in the gut.

While the use of invention methods and materials to evaluate the ability of compounds to enhance oral availability has been described in considerable detail, the invention is not limited to this specific application. Any suitable cell or tissue wherein influx or efflux of materials is of importance can be evaluated in this way. Thus, neuronal tissue can be evaluated by its ability to take up radiolabeled 2-deoxyglucose, since this material is known to be transported into neurons that are electrically active. Similarly, the release of a prelabeled neurotransmitter from cells in neurosystems contained on a brain slice can elucidate pathways of transmission. In addition, the ability of labeled compounds to be transported across the lung surface or the blood brain barrier can be evaluated.

Thus, any compartment that can be uniquely marked is the subject of study using the methods of the invention. Marking the serostat surface of a segment of gut and loading the radiolabel in the luminal compartment as described above is one example. In addition, the subdermal layer of skin can be marked with a scintillant and the labeled compound applied to the epidermis to visualize the transport through the skin. Brain extracellular spaces can be infiltrated with scintillant to mark the neurons; accumulation of radiolabeled 2-deoxyglucose intracellularly indicates neuronal activity. After a pulse of labeled compound has been washed out by the blood circulation, the marked cells will be visible if the mean-free path of the emission of the fixed isotope is in the 10–100 $\mu$ range. Conversely, intracellular compartments may be painted with scintillant, for example, via retrograde transport of colloidal scintillant particles. Isotopes with emissions having a short mean-free path, 0.5–5 $\mu$, are preferred in this instance. Thus, activity of every cell in a whole neural network may conveniently be examined in parallel.

In another application, strategies for making capillaries of tumors leakier to chemotherapeutics can be evaluated using this technique.

I claim:

1. A method to determine the location of a labeled compound as a function of time with respect to a compartmentalized biologically derived environment, which method comprises providing a cell, tissue or organelle marked with a scintillant in a first compartment of said cell, tissue or organelle to the exclusion of a second compartment of said biologically derived environment;

positioning said scintillant-marked cell, tissue or organelle on the observation stage of a microscope focused on the marked compartment;

contacting an unmarked compartment of said cell, tissue, organelle or biologically derived environment with a compound labeled with a beta-emitting radioactive isotope; and observing the appearance of scintillant emitted light, due to proximity of the labeled compound, in the marked compartment as a function of time.

2. The method of claim 1 which farther includes contacting the said unmarked compartment with a test substance along with said labeled compound and observing the appearance of scintillant-emitted light in the marked compartment as a function of time.

3. The method of claim 2 which further includes contacting the said unmarked compartment with said compound labeled with a beta-emitting radioactive isotope in the absence of said test substance;

observing the appearance of scintillant-emitted light in said marked compartment as a function of time; and comparing the observations of said scintillant-emitted light in the presence and absence of said test substance;

whereby an increase in scintillant-emitted light in the marked compartment or increase in the rate of appearance of scintillant-emitted light in the marked compartment in the presence as opposed to the absence of the test substance identifies the test substance as an enhancer of uptake of said labeled compound into the marked compartment, and whereby a decrease in scintillant-emitted light in the marked compartment or a decrease in the rate of appearance of scintillant-emitted in the marked compartment in the presence as opposed to the absence of the test substance identifies said test substance as a suppressor of uptake of said labeled compound into the marked compartment.

4. The method of claim 3 wherein said cells or tissue are gut epithelial cells or tissue or a surrogate cell or tissue model therefor.

5. The method of claim 4 wherein the surrogate cell or tissue model comprises Caco-2 cells grown as a continuous sheet on a membrane.

6. The method of claim 1 wherein said cells or tissue comprise brain cells or tissue and the labeled compound is a neurotransmitter.

7. The method of claim 1 wherein the first compartment is the intracellular space and the second compartment comprises the surroundings or wherein the first compartment is one side and the second compartment is the opposite side of an epithelial layer of cells.

8. The method of claim 2 wherein the first compartment is the intracellular space and the second compartment comprises the surroundings or wherein the first compartment is one side and the second compartment is the opposite side of an epithelial layer of cells.

9. The method of claim 3 wherein the first compartment is the intracellular space and the second compartment comprises the surroundings or wherein the first compartment is one side and the second compartment is the opposite side of an epithelial layer of cells.

10. A method to determine the location of a labeled compound as a function of time with respect to a compartmentalized biologically derived environment, which method comprises providing a cell, tissue or organelle marked with a scintillant in a first compartment of said cell, tissue or organelle to the exclusion of a second compartment of said biologically derived environment;

wherein said marked compartment has previously been provided or is simultaneously provided or is subsequently provided with a compound labeled with a beta-emitting radioactive isotope;

positioning said scintillant marked cell, tissue or organelle on a stage of a microscope focused on the marked compartment;

observing the diminution of scintillant-emitted light, due to proximity of the labeled compound, in said marked compartment as a function of time.

11. The method of claim 10 which further includes contacting the marked or unmarked compartment of said cell, tissue or organelle with a test substance; and observing the diminution of scintillant-emitted light in said marked compartment as a function of time.

12. The method of claim 11 which further includes observing the diminution of scintillant-emitted light in said marked compartment as a flnction of time in the absence of test substance;

comparing the time-dependent diminution of scintillant-emitted light in the marked compartment in the absence and presence of said test substance;

wherein a decrease in the amount or in the rate of diminution of scintillant-emitted light in the marked compartment in the presence as opposed to the absence of the test substance identifies said test substance as a suppressor of efflux from the marked compartment, and wherein an increase in the amount or in the rate of diminution of scintillant-emitted light in the marked compartment in the presence as opposed to the absence of the test substance identifies said test substance as an enhancer of efflux from the marked compartment.

13. The method of claim 10 wherein the first compartment is the intracellular space and the second compartment comprises the surroundings or wherein the first compartment is one side and the second compartment is the opposite side of an epithelial layer of cells.

14. The method of claim 11 wherein the first compartment is the intracellular space and the second compartment comprises the surroundings or wherein the first compartment is one side and the second compartment is the opposite side of an epithelial layer of cells.

15. The method of claim 12 wherein the first compartment is the intracellular space and the second compartment comprises the surroundings or wherein the first compartment is one side and the second compartment is the opposite side of an epithelial layer.

16. The method of claim 12 wherein said cells or tissue are gut epithelial cells or tissue or a surrogate cell or tissue model therefor.

17. The method of claim 16 wherein the surrogate cell or tissue model comprises Caco-2 cells grown as a continuous sheet on a membrane.

18. The method of claim 10 wherein said cells or tissue comprise brain cells or tissue and the labeled compound is a neurotransmitter.

* * * * *